(12) United States Patent
Finnegan (10) Patent No.: US 9,994,879 B2
(45) Date of Patent: Jun. 12, 2018

(54) METHOD OF PRODUCING FORMIC ACID

(71) Applicant: VERDANT BIOPRODUCTS LIMITED, Milton Keynes (GB)

(72) Inventor: Irene Finnegan, Milton Keynes (GB)

(73) Assignee: VERDANT BIOPRODUCTS LIMITED, Milton Keynes (GB)

( * ) Notice: Subject to any disclaimer, the term of this patent is extended or adjusted under 35 U.S.C. 154(b) by 0 days. days.

(21) Appl. No.: 15/288,518

(22) Filed: Oct. 7, 2016

(65) Prior Publication Data

US 2017/0044579 A1    Feb. 16, 2017

Related U.S. Application Data

(60) Division of application No. 14/718,859, filed on May 21, 2015, now Pat. No. 9,499,843, which is a continuation of application No. 14/232,724, filed as application No. PCT/GB2012/051690 on Jul. 13, 2012, now Pat. No. 9,040,281.

(30) Foreign Application Priority Data

Jul. 15, 2011    (GB) .................................. 1112231.4

(51) Int. Cl.
| | |
|---|---|
| *C12N 9/02* | (2006.01) |
| *C12P 7/64* | (2006.01) |
| *C12P 7/40* | (2006.01) |
| *C12N 1/20* | (2006.01) |
| *C12P 7/52* | (2006.01) |
| *C12P 7/54* | (2006.01) |
| *C12R 1/02* | (2006.01) |

(52) U.S. Cl.
CPC .............. *C12P 7/6409* (2013.01); *C12N 1/20* (2013.01); *C12N 9/0008* (2013.01); *C12P 7/40* (2013.01); *C12P 7/52* (2013.01); *C12P 7/54* (2013.01); *C12P 7/6436* (2013.01); *C12R 1/02* (2013.01); *Y02P 20/52* (2015.11)

(58) Field of Classification Search
None
See application file for complete search history.

(56) References Cited

U.S. PATENT DOCUMENTS

| | | | | |
|---|---|---|---|---|
| 7,432,095 | B2 * | 10/2008 | Nanba .................. | C12N 9/0008 435/190 |
| 9,040,281 | B2 * | 5/2015 | Finnegan ............. | C12N 9/0008 435/243 |
| 9,347,076 | B2 | 5/2016 | Liew et al. | |
| 9,499,843 | B2 * | 11/2016 | Finnegan ............. | C12N 9/0008 |
| 2010/0151543 | A1 * | 6/2010 | Reeves .................... | C12P 7/04 435/160 |
| 2014/0154755 | A1 | 6/2014 | Simpson et al. | |
| 2014/0193871 | A1 | 7/2014 | Chen et al. | |
| 2016/0030884 | A1 | 2/2016 | Wawrousek et al. | |
| 2016/0348017 | A1 * | 12/2016 | Finnegan .................. | C12P 5/00 |
| 2016/0348137 | A1 * | 12/2016 | Finnegan .................. | C12P 7/62 |
| 2017/0233773 | A1 * | 8/2017 | Finnegan .................. | C12P 7/24 435/147 |

FOREIGN PATENT DOCUMENTS

| | | | |
|---|---|---|---|
| KR | 2004/009875 | * | 1/2004 |
| WO | 2008070561 A2 | | 6/2008 |
| WO | 2010115054 A2 | | 10/2010 |
| WO | 2013050367 A2 | | 4/2013 |

OTHER PUBLICATIONS

Crable, B. et al. Formate Formation and Formate Conversion in Biological Fuels Production. Enzyme Research Article ID 532536, 2011. (Year: 2011).*
Azuma et al.; "Whole-genome analyses reveal genetic instability of Acetobacter pasteurianus"; Chemical Abstract; Document No. XP-002691298; Apr. 2009; 1 Page.
Chemler et al. "Biosynthesis of Isoprenoids, Polyunsaturated Fatty Acids and Flavonoids in *Saccharomyces cerevisiae*" Microbial Cell Factories; 5:20 (2006) 10 Pages.
Cleenwreck et al. "Polyphasic Taxonomy of Acetic Acid Bacteria: An Overivew of the Currently Applied Methodology" International Journal of Food Microbiolog; 125, 2-14 (2008; 14 Pages.
Crable et al. "Formate Formulation and Formate Conversion in Biological Fuels Production" Enzyme Research; vol. 2011; Article ID 532536, 8 Pages.
International Search Report of the International Searching Authority for International Application No. PCT/GB2012/051690; International Filing Date: Jul. 13, 2012; dated Jan. 31, 2013.
Lu et al. "Overproduction of Free Fatty Acids in *E. coli*: Implications for Biodiesel Production" Metabolic Engineering; vol. 10; (2008); pp. 333-339.
Matsushita K. et al. "Survival and Death in Bacteria", 2005. Japan, ISBN: 81-7736-236-4. pp. 169-181.
Reda et al. "Reversible Interconversion of Carbon Dioxide and Formate by an Electroactive Enzyme" PNAS; vol. 105; No. 31; Aug. 5, 2008; pp. 10654-10658.
Tanaka et al. "Separation of Aliphatic Carboxylic Acids by Ion-Exclusion Chromatography Using a Weak-Acid Eluent" Journal of Chromatography, 361 (1986); pp. 151-160.
Tishkov et al. "Catalytic Mechanism and Application of Formate Dehydrogenase" Biochemistry (Moscow), vol. 69; No. 11; (2004); pp. 1252-1267 Translated from Biokhimiyal vol. 69; No. 11; (2004); pp. 1537-1554.

* cited by examiner

*Primary Examiner* — Ralph J Gitomer
(74) *Attorney, Agent, or Firm* — Cantor Colburn LLP (57) ABSTRACT

The invention relates to a micro-organism comprising a hydrogenase enzyme system which is capable of converting carbon dioxide into formic acid and a second enzyme system which is capable of converting formic acid into aliphatic carboxylic acids having a chain length of five or more carbon atoms. Also described are various methods for producing oil, as well as other aspects of the invention.

19 Claims, 4 Drawing Sheets

Tank System 1

Figure 3

Tank System 2

Figure 4

METHOD OF PRODUCING FORMIC ACID

CROSS-REFERENCE TO RELATED APPLICATIONS

This Application is a divisional of U.S. Ser. No. 14/718,859, filed May 21, 2015, issued as U.S. Pat. No. 9,499,843, which is a continuation of U.S. Ser. No. 14/232,724, filed Jan. 14, 2014, issued as U.S. Pat. No. 9,040,281, which is the U.S. National Stage Application of International Application PCT/GB2012/051690, filed Jul. 13, 2012, which claims priority from Great Britain Patent Application No. 1112231.4, filed Jul. 15, 2011, all of which are incorporated by reference in their entirety.

FIELD OF THE INVENTION

The present invention relates to a micro-organism which is capable of converting carbon dioxide to formic acid which is then converted into aliphatic carboxylic acids of longer chain length. Particular enzyme systems in the micro-organism are responsible for these reactions. Further aspects of the invention relate to methods of producing formic acid and the aliphatic carboxylic acids, and the aliphatic carboxylic acids themselves.

BACKGROUND TO THE INVENTION

Over recent years, there has been increasing concern over the consumption of fossil fuels and the production of greenhouse gases. One way to reduce the globe's reliance on fossil fuels has been the development of biofuels from renewable sources. Biofuels such as biodiesel and bioethanol are considered to be cleaner and more environmentally friendly alternatives to fossil fuels.

Although biofuels may help in reducing green house emissions, they are not without problems. A controversial aspect is the "food for fuel" problem where the demand for energy crops has been perceived as pushing up the prices of grain commodities. Another serious drawback is the damage caused to ecologically sensitive ecosystems, such as rain forests, where the planting of energy crops such as soya and palm has caused large scale destruction.

The biofuels industry is turning to second and third generation biofuels to alleviate these issues. The production of fuels by micro-organisms (1) and the use of waste substrates (2) are important areas of research.

The conversion of carbon dioxide to fuel molecules is known. Carbon dioxide can be converted chemically (3), electrochemically (4), and either directly (5) or indirectly (6) by micro-organisms. Products such as formic acid, formate, methanol, formaldehyde, ethylene, methane and oxalic acid have been noted. However, these micro-organisms cannot convert carbon dioxide via formic acid into a longer chain energy source such as aliphatic carboxylic acids.

In US 2012003705, the conversion of carbon dioxide to biomass is described (7) and then the further processing of the biomass to a range of commercially useful molecules. However, this is not done through the steps of fixing carbon dioxide to formic acid and then converting the formic acid to aliphatic carboxylic acids.

Previous attempts at using carbon dioxide as a carbon substrate to produce fuel molecules have had limitations. Carbon dioxide and its aqueous ions bicarbonate and carbonate are inherently stable and the Gibbs free energy of formation are the most electronegative of the carbon molecules. To convert carbon dioxide to fuel molecules requires a large input of energy (heat), extreme conditions (pressure) and highly reactive chemicals (catalysts). Yields are often poor and the rates of reaction slow. Chemical approaches to the direct use of carbon dioxide are generally not considered to be economically viable. Likewise, the initial production of biomass by chemolithotrophic bacteria is not widely practised due to cost constraints of growth and downstream processing.

Electro-catalysis has also had limited success. Outcomes have been limited by the poor solubility of carbon dioxide in water (0.033M) and the energetic requirements of a reaction with a strong electronegative potential (E0=−0.61V). Electro-catalysis is also a costly technology requiring high quality metals for electrode surfaces. Production of longer chain products have been described in terms of Fischer Tropsch type reactions (8), but again chains are limited in length. Photoreduction on irradiated semi-conductor surfaces produces carbon monoxide, formate, methanol, methane, formaldehyde, oxalic acid and glyoxal. Again this is a costly technology with low yields.

While enzymes such as bacterial formate dehydrogenase are known to reduce carbon dioxide to formate (9), the forward reaction (oxidation of formate to carbon dioxide) is generally favoured because NADPH is required to drive the reaction and the reduction potential of NADP is more positive than that of carbon dioxide. Such a reaction also requires electron donor and acceptor molecules. Tungsten containing enzymes from Syntrophotobacterium fumioxidans (10) are able to carry out this reaction but require absorption onto an electrode surface for the electro-catalytic system to function efficiently. Further, longer fuel molecules are not produced.

The present invention is an improvement compared to the prior art in that carbon dioxide can be converted to an initial platform molecule (formic acid) and then assembled into longer chains in a rapid format that does not require fermentation or the generation and processing of biomass. This improves on known methods such as US2012/0003705 (11), which requires the production of biomass and recycling of electron donors and acceptors, and US 2010/03170741A1 (12), US 2012/0003706A1 (13), US2012/003707A (14) and US2012/0034664A1 (15) which all require fermentative processes.

SUMMARY OF THE INVENTION

A new micro-organism has been isolated by the inventor of this application which is capable of fixing carbon dioxide and converting it into an aliphatic carboxylic acid energy source. Therefore, in general, the invention relates to such a micro-organism comprising a hydrogenase enzyme system which can convert carbon dioxide into formic acid. The micro-organism also comprises a second enzyme system which can convert formic acid into aliphatic carboxylic acids having a chain length of five or more carbon atoms. This means that the carboxylic acids that can be produced have five or more carbon atoms in total in the compound. Additionally, the second enzyme system can also produce aliphatic carboxylic acids having a chain length of two, three and four carbon atoms. These shorter chain carboxylic acids are converted to aliphatic carboxylic acids having a chain length of five or more carbon atoms.

The micro-organism isolated by the inventor, an *Acetobacter lovaniensis*, is suitable for the production of oils on a commercial basis. This micro-organism uses carbon dioxide as its sole source of carbon and produces carboxylic acids of various lengths. The fact that the micro-organism uses carbon dioxide as its sole carbon source means that oil production is much more affordable than for other micro-organisms which have to be supplied with a hydrocarbon substrate to perform the same task (16, 17, 18). The use of such a micro-organism to convert carbon dioxide to a combustible fuel is of commercial value. Further, since the micro-organism does not require a hydrocarbon substrate, the need for the production of energy crops is removed.

The invention improves on current methods in that carbon dioxide is converted to a liquid fuel product without the need for fermentation or production and processing of biomass. Additionally, the conversion of carbon dioxide to fuel molecules is a very attractive option in that is both a free source of renewable carbon and its sequestration has positive effects for the environment.

Further advantages associated with the isolated micro-organism are that:

1) it is a non-pathogenic organism and is rated Class 1;
2) it does not require special growth conditions or large growth volumes as would be required for algae;
3) it has a robust hydrogenase enzyme system;
4) oil is synthesised external to the cell and is therefore easier to harvest and adapt to a commercial manufacturing process;
5) the oil produced consists mostly of long chain carboxylic acids. This oil can be used directly as a source of energy by combustion, or used as a feed stock in a number of industries such as in the production of biodiesel, detergents and various oleo chemicals;
6) the enzyme system will function in oil-water emulsions which are described as a novel route of manufacture in that the oil in the emulsion acts as a primer for chain building and increases the solubility of carbon dioxide in the reaction media; and
7) the enzyme system operates without the need to produce and process biomass.

Other aspects of the invention relate to methods of producing formic acid and the aliphatic carboxylic acid energy source, and the energy source itself.

These and further aspects of the invention will be described in more detail below.

DETAILED DESCRIPTION OF THE INVENTION

In one aspect of the invention, there is provided a micro-organism comprising a hydrogenase enzyme system which is capable of converting carbon dioxide into formic acid and a second enzyme system which is capable of converting formic acid into aliphatic carboxylic acids having a chain length of five or more carbon atoms.

The micro-organism may be any suitable micro-organism as long as it is capable of converting carbon dioxide into formic acid and then converting the formic acid into aliphatic carboxylic acids having a chain length of five or more carbon atoms. Preferably, the micro-organism is a prokaryote. More preferably, the micro-organism is a bacterium. In one embodiment, the micro-organism is lithotrophic. A lithotroph is an organism that uses an inorganic substrate (usually of mineral origin) to obtain reducing equivalents for use in biosynthesis (e.g., carbon dioxide fixation) or energy conservation via aerobic or anaerobic respiration. The micro-organism may be lithoautotrophic. A lithoautotroph is able to use carbon dioxide from the air as a carbon source. The micro-organism may use carbon dioxide as the sole source of carbon. The micro-organism may be chemolithotrophic. Chemolithotrophs use inorganic compounds for aerobic or anaerobic respiration. The energy produced by the oxidation of these compounds is enough for ATP production. Some of the electrons derived from the inorganic donors also need to be channeled into biosynthesis. In one embodiment, the micro-organism is chemolithoautotrophic.

The terms "lithotrophic", "lithoautotrophic", "chemolithotrophic" and "chemolithoautotrophic" used above are well known to those skilled in the art and have a precise meaning which is widely recognised. As a result, a skilled person would readily be able to determine whether a particular micro-organism, such as a bacterium, falls within the definition of one or more of these terms. Further, a skilled person could also test any micro-organisms of interest to determine whether they were classed in one or more of these categories. A skilled person could also test a micro-organism to see if it can produce an oil of aliphatic carboxylic acids having a chain length of five or more carbon atoms. Suitable methods for conducting such tests are well known to those skilled in the art.

In one embodiment, the micro-organism is an aerobic micro-organism. Again, it is well within the capabilities of a person skilled in the art to determine whether a particular micro-organism is an aerobic micro-organism. In the context of the present invention, the micro-organism, and more particularly the micro-organism's enzyme systems, produce aliphatic carboxylic acids under aerobic conditions, i.e. the presence of oxygen is tolerated in the reactions that produce the aliphatic carboxylic acids.

Where the micro-organism is a bacterium, the micro-organism may be any suitable bacterium which comprises a hydrogenase enzyme system capable of converting carbon dioxide to formic acid and a second enzyme system which is capable of converting formic acid into aliphatic carboxylic acids having a chain length of five or more carbon atoms. Preferably, the bacterium is an *Acetobacter* species. In one particular embodiment, the micro-organism is *Acetobacter lovaniensis*. The micro-organism may be similar to the *Acetobacter* strain having accession number NCIMB 41808 (deposited at NCIMB Ltd. (Ferguson Building, Craibstone Estate, Bucksburn, Aberdeen, AB21 9YA) on 12 Jan. 2011 under the provisions of the Budapest Treaty; hereinafter referred to as strain FJ1). The term "similar to" means a micro-organism which is functionally equivalent to FJ1. The micro-organism should have a hydrogenase enzyme system which is capable of converting carbon dioxide into formic acid and should be able to grow under the same conditions as FJ1. Further, the micro-organism should comprise the same or similar enzymatic pathways for producing aliphatic carboxylic acids having a chain length of five or more carbon atoms. The micro-organism may have at least about 60% sequence identity to FJ1. In some embodiments, the micro-organism may have at least about 65%, at least about 70%, at least about 75% or at least about 80% sequence identity to FJ1. Preferably, the micro-organism should have at least about 85%, at least about 90%, at least about 93%, at least about 95%, at least about 97%, at least about 98%, or at least about 99% sequence identity to FJ1. Methods for determining sequence identity between different micro-organisms are well known to those skilled in the art. For example, 16S rDNA analysis can be used. Detailed information regarding the culturing of FJ1 is given below. Therefore, it is well within the capabilities of a person skilled in the art to determine whether a micro-organism is similar to FJ1. In one embodiment, the micro-organism is FJ1.

In one particular embodiment, the micro-organism may be a recombinant micro-organism, i.e., a genetically engineered micro-organism. The micro-organism may comprise a nucleotide sequence (e.g. DNA) from another species of micro-organism. In particular, the micro-organism may comprise a heterologous gene or genes encoding the hydrogenase enzyme system. The heterologous gene or genes may be operatively linked to a heterologous promoter or to a promoter of the micro-organism. The heterologous gene or genes may be part of a plasmid (22). The heterologous gene or genes will be expressed in the micro-organism to produce a functional hydrogenase enzyme system allowing the micro-organism to convert carbon dioxide to formic acid. Suitable methods for introducing nucleotide sequences (e.g. DNA) of interest into micro-organism host cells are well known to those skilled in the art (For example, see Sambrook, J. and Russell, D. Molecular Cloning: A Laboratory Manual. Cold Spring Harbor Laboratory Press, US).

Alternatively, the micro-organism may be a naturally occurring micro-organism. This is a micro-organism which has not been genetically altered or modified.

In one embodiment, the micro-organism may be derived from FJ1. The term "derived from" means that FJ1 can be modified or mutated to produce further micro-organisms according to the invention. For example, genes may be inserted or removed from FJ1. Micro-organisms which are derived from FJ1 should be functionally equivalent to FJ1 and should have a hydrogenase enzyme system which is capable of converting carbon dioxide into formic acid. Further, the derived micro-organisms should be able to grow under the same conditions as FJ1. Furthermore, the derived micro-organisms should comprise the same or similar enzymatic pathways for producing aliphatic carboxylic acids having a chain length of five or more carbon atoms. The derived micro-organisms can produce aliphatic carboxylic acids in the same way as FJ1. In some embodiments, micro-organisms may be derived by repeatedly culturing and selecting micro-organisms in an artificial selection process.

The hydrogenase enzyme system can be any suitable enzyme system which is capable of converting carbon dioxide into formic acid. The hydrogenase enzyme system catalyses the conversion of carbon dioxide to formic acid. The hydrogenase enzyme system oxidises hydrogen to generate the electrons to reduce carbon dioxide to formic acid, for example, using the following reaction:

$$CO_2 + H_2 \rightarrow HCOOH$$

Generally, catalysis of the conversion of carbon dioxide to formic acid takes place in solution as carbon dioxide is soluble. In solution, carbon dioxide is reversibly converted to carbonic acid ($H_2CO_3$). Depending on the pH of the solution, the carbonic acid will normally be present as bicarbonate ($HCO_3^-$) or carbonate ($CO_3^{2-}$). Therefore, the conversion of carbon dioxide to formic acid by the hydrogenase enzyme system of the present invention also encompasses the conversion of bicarbonate and/or carbonate to formic acid. In other words, carbonate and bicarbonate are considered to be forms of carbon dioxide in the present invention. Bicarbonate and/or carbonate salts (such as sodium bicarbonate or sodium carbonate) may be added to solution to increase the level of these salts. However, this is not preferred as the salt ions (e.g. sodium ions) may form soap when the aliphatic carboxylic acids are produced.

As indicated above, carbon dioxide is preferably the sole source of carbon. Preferably, the carbon dioxide is converted directly from carbon dioxide to formic acid without the formation of any stable intermediates. In other words, the reaction occurs in a single step. Carbonate and bicarbonate are to be considered as forms of carbon dioxide which are in solution and are not intermediates. Therefore, the dissolution of carbon dioxide to carbonate and bicarbonate ions in solution and then to formic acid is considered to be direct conversion. On the other hand, conversion of carbon dioxide (or carbonate and/or bicarbonate ions) to methanol and then to formic acid is not considered to be direct conversion as a methanol intermediate is produced.

In some embodiments, the starting reactants for producing formic acid are water and carbon dioxide. In preferred embodiments, no other reactants are necessary to produce formic acid other than carbon dioxide and water. This does not, however, rule out the possibility that other components will be present in the initial reaction mixture. For example, an oxidising agent may be present to speed up the initiation of the reactions. Such other components are not reactants in the production of formic acid.

The hydrogenase enzyme system does not require electron acceptor and donor molecules in order to produce formic acid. For example, molecules such as NADP and NADPH are not required for the reaction to proceed. In fact, all the reactions to produce the aliphatic carboxylic acids having a chain length of five or more do not require electron acceptor or donor molecules.

The hydrogenase enzyme system does not use fermentation to produce formic acid. Further, neither does the second enzyme system use fermentation to produce the aliphatic carboxylic acids. Fermentation is the conversion of organic compounds such as carbohydrates into other compounds through biochemical processes involving electron acceptors and/or donors.

The hydrogenase enzyme system does not require biomass to produce formic acid. Therefore, no biomass needs to be provided to the micro-organism in order for aliphatic carboxylic acids to be produced. Biomass is biological organic material from plants or animals that can be converted to an energy source.

In the present invention, an electrochemical process such as electrocatalysis does not need to be used to convert carbon dioxide to formic acid and then to aliphatic carboxylic acids. An electrochemical process is a chemical reaction which take place in a solution at the interface of an electron conductor (a metal or a semiconductor) and an ionic conductor (the electrolyte), and which involves electron transfer between the electrode and the electrolyte or species in solution.

The hydrogenase enzyme system is preferably oxygen tolerant. This means that the hydrogenase enzyme system can tolerate relatively high levels of oxygen without damaging the enzyme system or affecting the activity of the enzyme system. Preferably, the hydrogenase enzyme system can function at an oxygen level of more than about 10%, more preferably, at an oxygen level of more than about 15%, and even more preferably, at an oxygen level of between about 20% and about 21%, e.g. at the level of oxygen found in the atmosphere (about 20.95%). Many hydrogenase enzymes are sensitive to the presence of oxygen and effectively stop working when oxygen is present. Preferably, the hydrogenase enzyme system is extracellular, i.e. outside the cell of the micro-organism. In other words, the hydrogenase enzyme system is positioned outside the cell membrane. It is orientated extracellularly. Preferably, the hydrogenase enzyme system is completely extracellular so that it is not attached to the micro-organism in any way, for example, by being attached to the cell membrane of the micro-organism. This advantageously allows formic acid formation to take place outside the cell of the micro-organism. The hydrogenase enzyme system is preferably functional between pH 3.0 and 8.5 and, more preferably, between pH 3.5 and 4.5. Further, the hydrogenase enzyme system is preferably functional between 5° C. and 60° C. and, more preferably, between 15° C. and 20° C.

The hydrogenase enzyme system may comprise one or more enzymes, in addition to the hydrogenase enzyme, to aid in the conversion of carbon dioxide to formic acid.

In one embodiment, the hydrogenase enzyme system is that of FJ1. In another aspect of the invention, there is provided the hydrogenase enzyme system of FJ1.

The micro-organism also comprises a second enzyme system which is capable of converting formic acid into aliphatic carboxylic acids having a chain length of five or more carbon atoms. The second enzyme system can be any suitable enzyme system which is capable of converting formic acid to aliphatic carboxylic acids having a chain length of five or more carbon atoms. The second enzyme system catalyses the conversion of formic acid to aliphatic carboxylic acids having a chain length of five or more carbon atoms. The aliphatic carboxylic acids can be used, e.g. in combustion, to produce energy.

Preferably, the second enzyme system is extracellular, i.e. outside the cell of the micro-organism. In other words, In other words, the second enzyme system is positioned outside the cell membrane. The second enzyme system is orientated extracellularly. This means that the conversion of formic acid to aliphatic carboxylic acids takes place extracellularly. This advantageously allows the aliphatic carboxylic acids to be easily extracted once produced by the micro-organism. Preferably, the second enzyme system is completely extracellular so that it is not attached to the micro-organism in any way, for example, by being attached to the cell membrane of the micro-organism.

In one embodiment, the second enzyme system is that of FJ1. In another aspect of the invention, there is provided the second enzyme system of FJ1.

As indicated above, the micro-organism may be a recombinant micro-organism. Therefore, the micro-organism may comprise a heterologous gene or genes encoding the second enzyme system. The heterologous gene or genes may be operatively linked to a heterologous promoter or to a promoter of the micro-organism. The heterologous gene or genes may be part of a plasmid. The heterologous gene or genes will be expressed in the micro-organism to produce a functional second enzyme system allowing the micro-organism to convert formic acid into aliphatic carboxylic acids having a chain length of five or more carbon atoms.

The precise nature of the aliphatic carboxylic acids that are produced by the micro-organism will depend, in part, on the length of time of the enzymatic reactions.

The aliphatic carboxylic acids produced by the micro-organism can have a chain length of five or more carbon atoms. Aliphatic carboxylic acids having a chain length of two, three and four carbon atoms are also produced by the micro-organism. The aliphatic carboxylic acids that are produced may be fatty acids. The aliphatic carboxylic acids may be short chain, medium chain or long chain aliphatic carboxylic acids, or a combination of these.

The term 'aliphatic' in the context of the aliphatic carboxylic acids means that the group attached to the —COOH group of the carboxylic acid comprises a chain of carbon atoms joined together to form the backbone of the group. This carbon backbone may be branched or unbranched. Preferably, the carbon backbone is unbranched. The carbon backbone may be saturated, mono-unsaturated (i.e. one carbon-carbon double bond) or poly-unsaturated (i.e. more than one carbon-carbon double bond). In one embodiment, the carbon backbone is mono-unsaturated. The carbon backbone is generally bonded to hydrogen atoms (other than the —COOH group). However, instead of one or more of the hydrogen atoms, the carbon backbone may be substituted with other groups such as OH groups. Preferably, the carbon backbone is unsubstituted, i.e. only hydrogen atoms are bonded to the carbon backbone other than the —COOH group.

The second enzyme system of the micro-organism which produces the aliphatic carboxylic acids from formic acid does so in a stepwise manner. A carbon atom is added one at a time to the carbon backbone of the aliphatic carboxylic acids. This produces a range of carboxylic acids having a carbon backbone of C2, C3, C4, C5, C6, C7, C8, C9, C10, etc. For example, starting with formic acid (C1), the second enzyme system can add a carbon atom to the carbon backbone of formic acid to produce acetic acid (C2). Then, the second enzyme system can add a carbon atom to the carbon backbone of acetic acid to produce propionic acid (C3). This process can continue so that sequentially butyric acid (C4), valeric acid (C5), hexanoic acid (C6), heptanoic acid (C7), octanoic acid (C8), nonanoic acid (C9), decanoic acid (C10), etc. can be produced. Therefore, the second enzyme system is capable of converting formic acid into an aliphatic carboxylic acid having a chain length of two or more carbon atoms, three or more carbon atoms, four or more carbon atoms, five or more carbon atoms, six or more carbon atoms, seven or more carbon atoms, eight or more carbon atoms, nine or more carbon atoms, ten or more carbon atoms, etc. The second enzyme system can catalyse the addition of a carbon atom (e.g. a $CH_2$ unit) to the carbon chain of aliphatic carboxylic acids.

In this way, the enzyme systems of the micro-organism can produce a range of different length aliphatic carboxylic acids. For example, the micro-organism may produce a range of aliphatic carboxylic acids having a carbon backbone length of between about 2 and about 24 carbon atoms, between about 3 and about 24 carbon atoms, between about 4 and about 24 carbon atoms or between about 5 and about 24 carbon atoms. Further, the micro-organism can produce a range of aliphatic carboxylic acids having a carbon backbone length of between about 6 and about 24 carbon atoms, between about 7 and about 24 carbon atoms, between about 8 and about 24 carbon atoms or between about 9 and about 24 carbon atoms. Additionally, the micro-organism can produce a range of aliphatic carboxylic acids having a carbon backbone length of between about 10 and about 24 carbon atoms, between about 11 and about 24 carbon atoms, between about 12 and about 24 carbon atoms or between about 13 and about 24 carbon atoms. When the micro-organism is cultured, the length of the hydrocarbon chain is likely to be longer if the micro-organism is cultured for longer since the enzyme systems will have been active for longer. The period for which the micro-organism is cultured determines the average chain length. In one embodiment, the aliphatic carboxylic acid content calculated as C18 is between about 70% and 90%. More preferably, the aliphatic carboxylic acid content calculated as C18 is about 80%.

Preferably, the aliphatic carboxylic acids produced by the micro-organism are combustible. Preferably, the aliphatic carboxylic acids produced by the micro-organism are in the form of an oil. This makes separation of the aliphatic carboxylic acids easier. The oil may be a semi-drying oil. Whether an oil is semi-drying can be evaluated from the iodine value. Standard methods of analysis are for example EN 14111. Preferably, the iodine value of the oil is 85-95 mg I/100 g. More preferably, the iodine value of the oil is 90-95 mg I/100 g. The aliphatic carboxylic acids may be mono-unsaturated.

Figure 1:
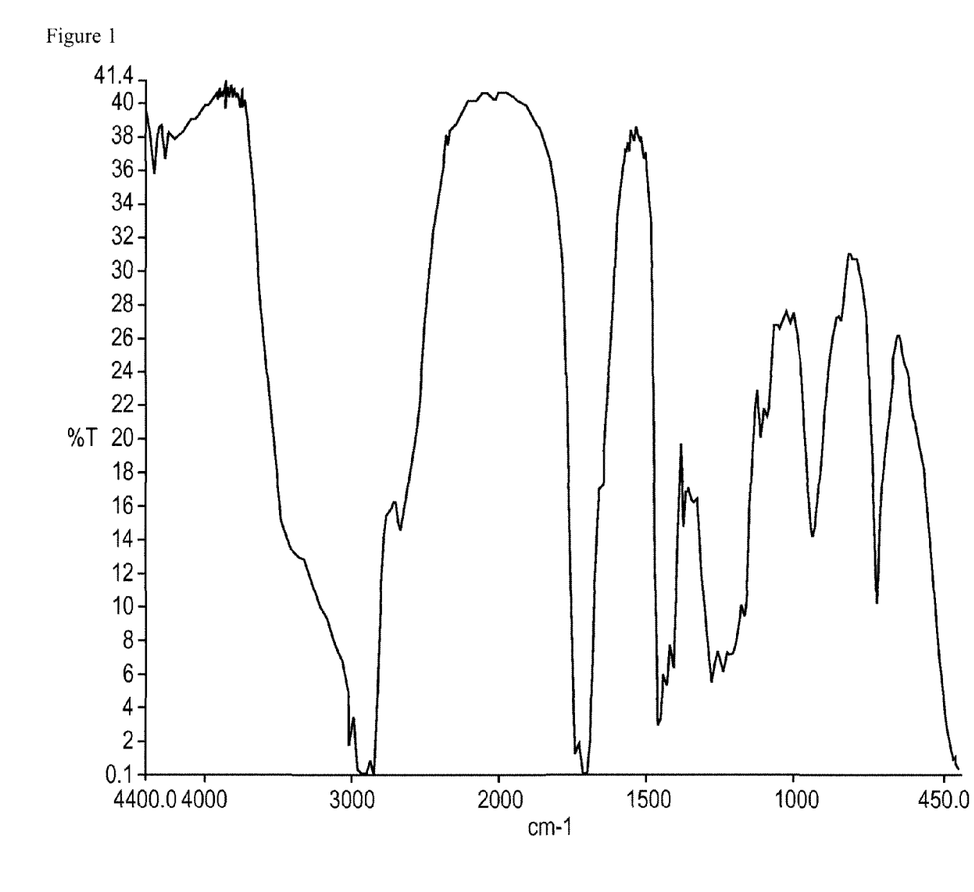
FIG. 1 is an infrared scan of an energy source produced by the micro-organism of the invention. The energy source is an oil product comprising aliphatic carboxylic acids and the infrared scan shows chemical features typical of an aliphatic carboxylic acid.

An infrared scan of aliphatic carboxylic acids produced by a micro-organism of the invention can be seen in FIG. 1. This shows that the sample, which is an oil, is made up of long chain carboxylic acids and is an aliphatic carboxylic acid.

The aliphatic carboxylic acids, once extracted, may have one or more of the following properties:

| Analysis | Typical Value | Method of Analysis |
|---|---|---|
| Ash g/100 g | 0.025-0.050 | ISO 3987 |
| Flash Point ° C. | >100 | EN ISO 3679 |
| Kinematic Viscosity cSt | | EN ISO 3104 |
| @ 20° C. | 70-75 | |
| @ 30° C. | 52-57 | |
| @ 40° C. | 47-52 | |
| @ 50° C. | 30-35 | |
| @ 60° C. | 20-25 | |
| @ 70° C. | 15-20 | |
| @ 80° C. | 10-15 | |
| @ 90° C. | 7-12 | |
| Viscosity Index | 55 | ASTM D2270 |
| Water Content g/100 g | <0.5 | EN ISO 12937 |
| Density kg/l @ 20° C. | 920-950 | EN ISO 12185 |
| Acid Value mg KOH/g | 140-160 | EN 14104 |
| Iodine Value mg I/100 g | 85-95 | EN 14111 |
| Copper Strip Corrosion | 1B | ASTM D849 |
| Oxidative Stability H | >48 hours | ASTM D2274 |
| Sulphur % m/m | <0.1 (typically 0.05) | ASTM D2622 |
| Peroxide Value meq/kg | <3 | AOAC 965.33 |
| Cetane Index | ~50 | ASTM D976 |
| Gross Calorific Value Mj/kg | >37 | ASTM D5865 |
| Sediment potential | <0.2 (typically 0.08) | ASTM D-6469 |

In some embodiments, the kinematic viscosity (cSt) at 40° C. may be 20-25. Further, the flask point may be more than 180° C.

It has been found that the oxidative stability of the aliphatic carboxylic acids is surprisingly high compared to other biofuels such as biodiesel. Normal biodiesel has an oxidative stability of about 30 minutes (when tested with ASTMD2274). The aliphatic carboxylic acids have an oxidative stability of more than 48 hours.

A typical composition for oils produced after different reaction lengths is shown below. These tables show the boiling point of the various fractions. So, when the aliphatic carboxylic acids are fractionated, the fractions are split up into bands and the boiling point of these fractions measured. For example, the first 10% of the aliphatic carboxylic acids when fractionated off will have a certain boiling point. The second 10% (i.e. 10-20% referred to below as 20%) will have another boiling point and so on.

Typical Distillation Range of a Heavier Fraction Produced by Reaction for 1.5 Hours

| Percentage Distillate | Boiling Point ° C. |
|---|---|
| Initial Boiling Point | 188 |
| 10% | 232 |
| 20% | 256 |
| 30% | 272 |
| 40% | 292 |
| 50% | 306 |
| 60% | 321 |
| 70% | 332 |
| 80% | 359 |
| 90% | 391 |
| Final Boiling Point | 395 |

Typical Distillation Range of a Lighter Fraction Produced by Reaction for 0.5 Hours

| Percentage Distillate | Boiling Point ° C. |
|---|---|
| Initial Boiling Point | 99 |
| 10% | 113 |
| 20% | 115 |
| 30% | 118 |
| 40% | 118 |
| 50% | 119 |
| 60% | 121 |
| 70% | 129 |
| 80% | 308 |
| 90% | 370 |
| Final Boiling Point | 395 |

As discussed above, the micro-organism can be produced recombinantly. Accordingly, in a further aspect of the invention, there is provided a method of producing a micro-organism, the method comprising the step of inserting a gene or genes encoding a hydrogenase enzyme system capable of converting carbon dioxide to formic acid into a micro-organism, wherein the gene or genes are expressed by the micro-organism.

The method further comprises the step of inserting a gene or genes encoding a second enzyme system which is capable of converting formic acid into aliphatic carboxylic acids having a chain length of five or more carbon atoms, wherein the gene or genes are expressed by the micro-organism.

Also provided is a method of producing a micro-organism, the method comprising the step of inserting a gene or genes encoding a hydrogenase enzyme system capable of converting carbon dioxide to formic acid into a micro-organism, wherein the micro-organism comprises a second enzyme system which is capable of converting formic acid into aliphatic carboxylic acids having a chain length of five or more carbon atoms, and wherein the gene or genes are expressed by the micro-organism.

Also provided is a method of producing a micro-organism, the method comprising the step of inserting a gene or genes encoding a second enzyme system which is capable of converting formic acid into aliphatic carboxylic acids having a chain length of five or more carbon atoms into a micro-organism, wherein the micro-organism comprises a hydrogenase enzyme system capable of converting carbon dioxide to formic acid, and wherein the gene or genes are expressed by the micro-organism.

The description above relating to the micro-organism of the invention, and the preferable features thereof, are equally applicable to the methods for producing the micro-organism. For example, the particular features relating to the nature of the micro-organism are also applicable to the methods.

In another aspect, the invention provides a method of producing aliphatic carboxylic acids, the method comprising culturing a micro-organism comprising a hydrogenase enzyme system which is capable of converting carbon dioxide to formic acid and a second enzyme system which is capable of converting formic acid into aliphatic carboxylic acids having a chain length of five or more carbon atoms.

As indicated above, aliphatic carboxylic acids having a range of carbon backbone lengths can be produced. Preferably, aliphatic carboxylic acids having a carbon backbone length of between about 5 and about 24 carbon atoms are produced. More preferably, aliphatic carboxylic acids having a carbon backbone length of between about 10 and about 24 carbon atoms are produced. More preferably still, aliphatic carboxylic acids having a carbon backbone length of between about 16 and about 20 carbon atoms are produced. In one embodiment, the aliphatic carboxylic acids have a carbon backbone length of more than 2, 3, 4, 5, 6, 7, 8, 9 or 10. Further, the aliphatic carboxylic acids may have a carbon backbone length of less than 25.

Alternatively, the aliphatic carboxylic acid content calculated as C18 is between about 70% and 90%. More preferably, the aliphatic carboxylic acid content calculated as C18 is about 80%.

Any suitable conditions may be used for culturing the micro-organism. The micro-organism may be cultured at a pH of between about 3.0 and about 8.5 and, more preferably, between about 3.5 and about 4.5. Further, the micro-organism may be cultured at a temperature of between about 5° C. and about 60° C. and, more preferably, between about 15° C. and about 20° C.

The culture solution will contain carbon dioxide. This can be carbon dioxide which has dissolved from the air. Preferably, carbon dioxide gas is bubbled through the culture solution to increase the level of carbon dioxide available to react. When carbon dioxide is bubbled through the culture solution, it can come from a compressed gas cylinder. Alternatively, it can be contained in gas from another source. For example, waste gases from combustion can be bubbled through the culture medium.

In some embodiments, carbon dioxide (e.g. waste gases from combustion) can be bubbled through the culture solution (which may optionally contain a carbon dioxide sequestering agent) before the addition of the micro-organism.

Preferably, the micro-organism is cultured with carbon dioxide as the sole source of carbon.

The culture medium in which the culturing of the micro-organism takes place may be any suitable culture medium. Preferably, carbon dioxide is the sole source of carbon in the medium (as mentioned above $HCO_3^-$ and $CO_3^{2-}$ are considered to be soluble forms of carbon dioxide and are encompassed by the term carbon dioxide. The culture medium may comprise one or more of the following components: $KH_2PO_4$; $MgSO_4.7H_2O$; $CaCO_3$; $CuSO_4$; $FeCl_3$; $MnCl_3$; $MoCl_3$; and $ZnCl_3$. Further, these components may be present in the culture medium at the following concentrations:

| NUTRIENT | g/litre |
| --- | --- |
| $KH_2PO_4$ | 1.00 |
| $MgSO_4 \cdot 7H_2O$ | 0.10 |
| $CaCO_3$ | 0.10 |
| $CuSO_4$ | 0.10 |
| $FeCl_3$ | 0.01 |
| $MnCl_3$ | 0.01 |
| $MoCl_3$ | 0.01 |
| $ZnCl_3$ | 0.01 |

Preferably, the micro-organism is cultured in solution in an oil-water emulsion. This can be achieved by introducing some oil into the culture medium and agitating the oil-water mixture so that it forms an emulsion. For example, circulation of the reaction mixture can be used. It is thought that using an oil-water emulsion helps to increase the solubility of the carbon dioxide. It is also thought that this helps to keep the aliphatic carboxylic acids in solution so that their chain length can continue to increase.

Preferably, a carbon dioxide sequestering agent is introduced into the reaction mixture. This helps to increase the level of carbon dioxide in the reaction mixture/solution in order to maintain/increase the rate of reaction. Suitable carbon dioxide sequestering agents are well known to those skilled in the art and include alkalai compounds such as sodium hydroxide, potassium hydroxide, barium chloride, triethanolamine, diethanolamine, monoethanolamine, ammonia, methanol, sulfolane, polyethylene glycol ethers, polyethylene glycols, glycerol, and surfactants such as the Triton TX series. Some suitable carbon dioxide sequestering agents are described in Ortrud Ashenbrenner and Peter Styring (2010) (21). Preferably, the carbon dioxide sequestering agent is triethanolamine or polyethylene glycol. In some embodiments, the carbon dioxide sequestering agent is triethanolamine. In other embodiments, the carbon dioxide sequestering agent is a polyethylene glycol such as PEG 300. Advantageously, polyethylene glycols do not require a chemical reaction to release the carbon, dioxide, do not contain nitrogen which can potentially form NOX emissions on combustion, do not form soaps, and help to reduce the ash in the final product.

Preferably, an oxidising agent is introduced into the reaction mixture. This helps initiate the reaction process and speeds up the start of the reaction. Suitable oxidising agents include sodium hypochlorite and sodium hydroxide. The oxidising agent should be a mild oxidising agent. In one embodiment, bleach can be used the oxidising agent.

The method may further comprise the step of separating the aliphatic carboxylic acids.

In another aspect, the invention provides aliphatic carboxylic acids produced by the method described above.

In yet another aspect, the invention provides aliphatic carboxylic acids created from a series of condensation reactions between formic acid molecules.

As indicated above, aliphatic carboxylic acids having a range of carbon backbone lengths can be produced. Preferably, the aliphatic carboxylic acids have a carbon backbone length of between about 5 and about 24 carbon atoms. More preferably, the aliphatic carboxylic acids have a carbon backbone length of between about 10 and about 24. More preferably still, the aliphatic carboxylic acids have a carbon backbone length of between about 16 and about 20 carbon atoms. Alternatively, the aliphatic carboxylic acid content calculated as C18 is between about 70% and 90%. More preferably, the aliphatic carboxylic acid content calculated as C18 is about 80%.

Preferably, the aliphatic carboxylic acids are in the form of an oil. This makes separation of the aliphatic carboxylic acids easier. The oil may be a semi-drying oil. Preferably, the aliphatic carboxylic acids are mono-unsaturated.

The aliphatic carboxylic acids, once extracted, may have one or more of the following properties:

| Analysis | Typical Value |
| --- | --- |
| Ash g/100 g | 0.025-0.050 |
| Density @ 15° C. | 0.8483-0.8720 |
| Flash Point ° C. | >100 |

-continued

| Analysis | Typical Value |
| --- | --- |
| Kinematic Viscosity cSt | |
| @ 20° C. | 70-75 |
| @ 30° C. | 52-57 |
| @ 40° C. | 47-52 |
| @ 50° C. | 30-35 |
| @ 60° C. | 20-25 |
| @ 70° C. | 15-20 |
| @ 80° C. | 10-15 |
| @ 90° C. | 7-12 |
| Viscosity Index | 55 |
| Water Content g/100 g | 1 max (pref. <0.5) |
| Acid Value mg KOH/g | 140-160 |
| Iodine Value mg I/100 g | 85-95 |
| Copper Strip Corrosion | 1B |
| Oxidative Stability H | 48+ |
| Sulphur % m/m | <0.1 |
| Peroxide Value meq/kg | <3 |
| Cetane Index | ~50 |
| Gross Calorific Value Mj/kg | >37 |
| Sediment potential | <0.2 (typically 0.08) |

The invention also provides the use of the micro-organisms described above for producing aliphatic carboxylic acids.

In one embodiment, the enzymes responsible for converting carbon dioxide to formic acid and then to aliphatic carboxylic acids are extracellular of the micro-organism. These enzymes function regardless of whether the cells of the micro-organism are present. Therefore, in another aspect of the invention, there is provided a method for producing aliphatic carboxylic acids, the method comprising producing aliphatic carboxylic acids using a medium comprising a hydrogenase enzyme system which is capable of converting carbon dioxide into formic acid and a second enzyme system which is capable of converting formic acid to aliphatic carboxylic acids having a chain length of five or more carbon atoms.

The medium can be produced by culturing the micro-organism for a period of time to allow the enzyme systems to be produced in the medium. If desired, it is possible to produce a cell free extract which contains the enzymes but not the cells of the micro-organism. This can be done, for example, by removing the cells of the micro-organism from the medium after culturing, for example, by repeated ultrafiltration. Alternatively, rather than removing the cells of the micro-organism from the medium, the cells can be left in the medium but instead killed, for example, by introducing a disinfectant or antimicrobial agent into the medium. Alternatively, the micro-organisms can be left in the medium.

The method may further comprise preparing the medium before producing the aliphatic carboxylic acids using the medium.

Any suitable conditions can be used for producing the aliphatic carboxylic acids. For example, carbon dioxide and water are provided. The medium may have a pH of between about 3.0 and about 8.5 and, more preferably, between about 6.0 and about 7.0. Further, the medium may have a temperature of between about 5° C. and about 60° C. and, more preferably, between about 15° C. and about 20° C.

As with the first method, carbon dioxide is preferably used as the sole source of carbon, for example, by bubbling carbon dioxide gas through the reaction medium. Preferably, the reaction medium is an oil-water emulsion. Further, a carbon dioxide sequestering agent is preferably introduced into the reaction medium.

The method may further comprise the step of separating the aliphatic carboxylic acids.

In all embodiments of the aliphatic carboxylic acid production methods described above, once the aliphatic carboxylic acids have been produced, various optional steps may be carried out on the aliphatic carboxylic acids. For example, the methods may optionally comprise one or more of the following steps:

1) separating the aliphatic carboxylic acids;
2) filtering the aliphatic carboxylic acids;
3) blending the aliphatic carboxylic acids with a different fuel, preferably an oil fuel;
4) chemically modifying the carboxylic acids, for example, into ester, alcohols, ketones or aldehydes; and
5) distilling off certain fractions of the aliphatic carboxylic acids.

In another aspect, the invention provides aliphatic carboxylic acids produced by the methods described above.

One aspect of the invention also provides a medium comprising a hydrogenase enzyme system which is capable of converting carbon dioxide into formic acid and a second enzyme system which is capable of converting formic acid to aliphatic carboxylic acids having a chain length of five or more carbon atoms.

From the medium comprising a hydrogenase enzyme system which is capable of converting carbon dioxide into formic acid and a second enzyme system which is capable of converting formic acid to aliphatic carboxylic acids having a chain length of five or more carbon atoms, it is possible to isolate the enzymes contained therein using various techniques. For example, the enzymes could be separated using known techniques such as gel exclusion chromatography and selected based on their molecular sizes and activities.

The invention also provides use of a hydrogenase enzyme system which is capable of converting carbon dioxide into formic acid and a second enzyme system which is capable of converting formic acid to aliphatic carboxylic acids having a chain length of five or more carbon atoms for producing aliphatic carboxylic acids.

Further, the invention provides a method of producing aliphatic carboxylic acids, the method comprising converting carbon dioxide to formic acid and then converting formic acid to aliphatic carboxylic acids having a chain length of five or more carbon atoms, wherein the conversion reactions take place in an oil-water emulsion.

Preferred features of the above method are the same as for the method of producing aliphatic carboxylic acids above. For example, the features relating to the range of carbon backbone lengths that are produced, the temperature and pH at which the reactions are carried out, the carbon dioxide source, the carbon dioxide sequestering agent, the oxidising agent, etc. are preferred features for this method.

For example, the emulsion will contain carbon dioxide. This can be carbon dioxide which has dissolved from the air. Preferably, carbon dioxide gas is bubbled through the emulsion to increase the level of carbon dioxide available to react. When carbon dioxide is bubbled through the emulsion, it can come from a compressed gas cylinder. Alternatively, it can be contained in gas from another source. For example, waste gases from combustion can be bubbled through the emulsion.

In some embodiments, carbon dioxide (e.g. waste gases from combustion) can be bubbled through the emulsion (which may optionally contain a carbon dioxide sequestering agent).

Preferably, carbon dioxide is the sole source of carbon.

Preferably, a carbon dioxide sequestering agent is introduced into the emulsion. This helps to increase the level of carbon dioxide in the reaction mixture/solution in order to maintain/increase the rate of reaction. Suitable carbon dioxide sequestering agents are well known to those skilled in the art and include alkali compounds such as sodium hydroxide, potassium hydroxide, barium chloride, triethanolamine, diethanolamine, monoethanolamine, ammonia, methanol, sulfolane, polyethylene glycol ethers, polyethylene glycols, glycerol, and surfactants such as the Triton TX series. Some suitable carbon dioxide sequestering agents are described in Ortrud Ashenbrenner and Peter Styring (2010) (21). Preferably, the carbon dioxide sequestering agent is triethanolamine or polyethylene glycol. In some embodiments, the carbon dioxide sequestering agent is triethanolamine. In other embodiments, the carbon dioxide sequestering agent is a polyethylene glycol such as PEG 300. Advantageously, polyethylene glycols do not require a chemical reaction to release the carbon, dioxide, do not contain nitrogen which can potentially form NOX emissions on combustion, do not form soaps, and help to reduce the ash in the final product.

Preferably, an oxidising agent is introduced into the emulsion. This helps initiate the reaction process and speeds up the start of the reaction. Suitable oxidising agents include sodium hypochlorite and sodium hydroxide. The oxidising agent should be a mild oxidising agent. In one embodiment, bleach can be used the oxidising agent.

The method may further comprise the step of separating the aliphatic carboxylic acids or any one or more of the processing steps described above.

Additionally, the invention provides a method of producing aliphatic carboxylic acids having a chain length of five or more carbon atoms, the method comprising converting carbon dioxide to formic acid and then converting formic acid to aliphatic carboxylic acids having a chain length of five or more carbon atoms, wherein an oxidising agent is used to initiate the conversion of carbon dioxide to formic acid.

Preferred features of the above method are the same as for the methods of producing aliphatic carboxylic acids above. For example, the features relating to the range of carbon backbone lengths that are produced, the temperature and pH at which the reactions are carried out, the carbon dioxide source, the carbon dioxide sequestering agent, the emulsion, etc. are preferred features for this method.

For example, generally, the formic acid and aliphatic carboxylic acids will be produced in solution. The solution will contain carbon dioxide. This can be carbon dioxide which has dissolved from the air. Preferably, carbon dioxide gas is bubbled through the solution to increase the level of carbon dioxide available to react. When carbon dioxide is bubbled through the solution, it can come from a compressed gas cylinder. Alternatively, it can be contained in gas from another source. For example, waste gases from combustion can be bubbled through the solution.

In some embodiments, carbon dioxide (e.g. waste gases from combustion) can be bubbled through the solution (which may optionally contain a carbon dioxide sequestering agent).

Preferably, carbon dioxide is the sole source of carbon.

Preferably, a carbon dioxide sequestering agent is introduced into the solution. This helps to increase the level of carbon dioxide in the reaction mixture/solution in order to maintain/increase the rate of reaction. Suitable carbon dioxide sequestering agents are well known to those skilled in the art and include alkali compounds such as sodium hydroxide, potassium hydroxide, barium chloride, triethanolamine, diethanolamine, monoethanolamine, ammonia, methanol, sulfolane, polyethylene glycol ethers, polyethylene glycols, glycerol, and surfactants such as the Triton TX series. Some suitable carbon dioxide sequestering agents are described in Ortrud Ashenbrenner and Peter Styring (2010) (21). Preferably, the carbon dioxide sequestering agent is triethanolamine or polyethylene glycol. In some embodiments, the carbon dioxide sequestering agent is triethanolamine. In other embodiments, the carbon dioxide sequestering agent is a polyethylene glycol such as PEG 300. Advantageously, polyethylene glycols do not require a chemical reaction to release the carbon, dioxide, do not contain nitrogen which can potentially form NOX emissions on combustion, do not form soaps, and help to reduce the ash in the final product.

Preferably, the reactions take place in an oil-water emulsion.

The method may further comprise the step of separating the aliphatic carboxylic acids or any one or more of the processing steps described above.

The method of producing oil is "driven" in a novel way. The first step of the process is the reduction of carbon dioxide to produce formic acid. Formic acid is a reducing agent (redox potential −0.25). The first step of the reaction fixes carbon dioxide but also generates sufficient reducing equivalents to drive the next part of the process (chain building). The use of an "in situ" chemical battery could be used to drive other redox reactions. Formic acid (reductant) then reduces available carboxylic acids (oxidant), adding one carbon to a growing chain and releasing oxygen as $O_2$. This circumvents the need to add a reducing agent to drive the reaction, carbon and reducing equivalents being sequestered in the final product.

EXAMPLES

The invention will now be described in detail by way of example only with reference to the figures in which.

The following description is in no way limiting to the scope of the invention.

Overview

The following aspects of the invention will be discussed:
1) Properties of the bacterial culture;
2) Production of carbon building blocks (formic acid);
3) Assembly of building blocks into short, medium and long chain aliphatic carboxylic acids; and
4) The product.

The Bacterial Culture

The bacterial culture preferably has the following properties:

It is a chemolithotrophic, aerobic organism growing on carbon dioxide as its sole source of carbon.

It possesses an oxygen tolerant hydrogenase enzyme system that is extracellular. This enzyme system should be stable and active between pH 3.0 and 8.5 and between 5° C. and 60° C.

It possesses an extracellular enzyme component capable of assembling formic acid into short, medium and long chain hydrocarbon molecules with a carboxylic acid functionality.

It is able to form an oil like product with typical values as specified below. Oil should be synthesised extracellularly and physically separate to the top of the reaction media.

In one embodiment, the bacterium is *Acetobacter lovaniensis* FJ1.

Production of Carbon One Building Blocks (Formic Acid)

The micro-organism should reduce carbon dioxide to formic acid using a hydrogenase enzyme system. Hydrogen is oxidised to generate electrons to reduce carbon dioxide to formic acid as follows:

$$CO_2 + H_2 \rightarrow HCOOH$$

This enzyme system functions in a cell free extract which implies extracellular activity.

Assembly of Formic Acid into Short, Medium and Long Chain Hydrocarbons

The micro-organism should be capable of generating formic acid and forming more complex molecules by the stepwise addition of formic acid. High levels of formic acid are formed and a minimum level of 250 g per liter of formic acid equivalents is maintained. This is where the level of acidity is calculated as formic acid. Short chain aliphatic carboxylic acids form first.

| Volatile Acid | 5 Day Culture mg/l | 10 day culture mg/l |
|---|---|---|
| Acetic Acid (C2) | 152 | 619 |
| Propionic Acid (C3) | 406 | 1840 |
| Butyric Acid (C4) | 276 | 1220 |
| Valeric Acid (C5) | 272 | 1250 |
| Iso Butyric Acid (C4) | <50 | <50 |
| Iso Valeric Acid (C5) | <50 | <50 |

The presence of C2, C3, C4 and C5 aliphatic carboxylic acids implies stepwise addition of formic acid, since odd and even chain lengths are represented. Iso butyric and Iso valeric acid were either absent or below the level of detection demonstrating that straight chain aliphatic carboxylic acids were produced. The amount of any given aliphatic carboxylic acid increases with time.

The system is then held in equilibrium between the production of formic acid and the formation of larger molecules. At equilibrium, the quantity of oil generated (as measured by dry weight) is 5-10% of the acidity as measured as formic acid equivalents. Oil is then generated on a continuous basis by the removal of an oily layer at the air liquid interface and the addition of an equal volume of fresh media. The upper oily layer is pooled and concentrated.

The oil product consists of a mixture of carboxylic acids of varying chain lengths. The length of chain is adjusted by the rate of removal from the primary culture. Chain length and proportions of molecules generated are varied by adjusting the reaction conditions and the type of equipment used. Types of reactors that can be used include but are not limited to batch, continuous and semi-continuous. Reactor types include but are not limited to closed reactors, open reactors, paddle stirred, circulated, and gas lifted.

Production of oil can be on a semi-continuous basis. The organism is maintained in batch culture using a minimal media as detailed in the table below. This is the "stock culture".

| NUTRIENT | g/litre |
|---|---|
| KH$_2$PO$_4$ | 1.00 |
| MgSO$_4$·7H$_2$O | 0.10 |
| CaCO$_3$ | 0.10 |
| CuSO$_4$ | 0.01 |
| FeCl$_3$ | 0.01 |
| MnCl$_3$ | 0.01 |
| MoCl$_3$ | 0.01 |
| ZnCl$_3$ | 0.01 |

The pH of the media is adjusted to 4.0±0.2. The acidity in the stock culture is maintained at 20-25%, calculated as formic acid.

Before use in a reaction tank, the cell culture media is diluted 1/10 in water and held in an intermediate tank. This is the working culture.

Oil is produced in reaction tanks including but not limited to the tank systems described below. Sources of carbon dioxide include but are not limited to atmospheric carbon dioxide, carbonate, bicarbonate ions, waste waters containing carbonate or bicarbonate ions, compressed gas and exhaust gasses containing carbon dioxide.

Tank System 1

The reaction tank is a long narrow tank (FIG. 2) constructed from plastic or plastic coated material. Female connectors of a suitable size are set in the side of the tank to allow addition of media or removal of product. Typical dimension would be 5 units long by 1 to 1.5 units wide and 0.5 to 1.0 units deep. A partition is set in the tank ⅕ from one end of the tank. This partition is ⅘$^{th}$ the height of the tank. Circulating pumps with hoses are added to each partition. A sparge bar for re-circulation of contents can also be added to each partition. Compressed carbon dioxide can be additionally added to the reaction tank via a gas cylinder and line. A heater or heater lamp may be positioned over the smaller of the two sections of the tank.

Figure 2:
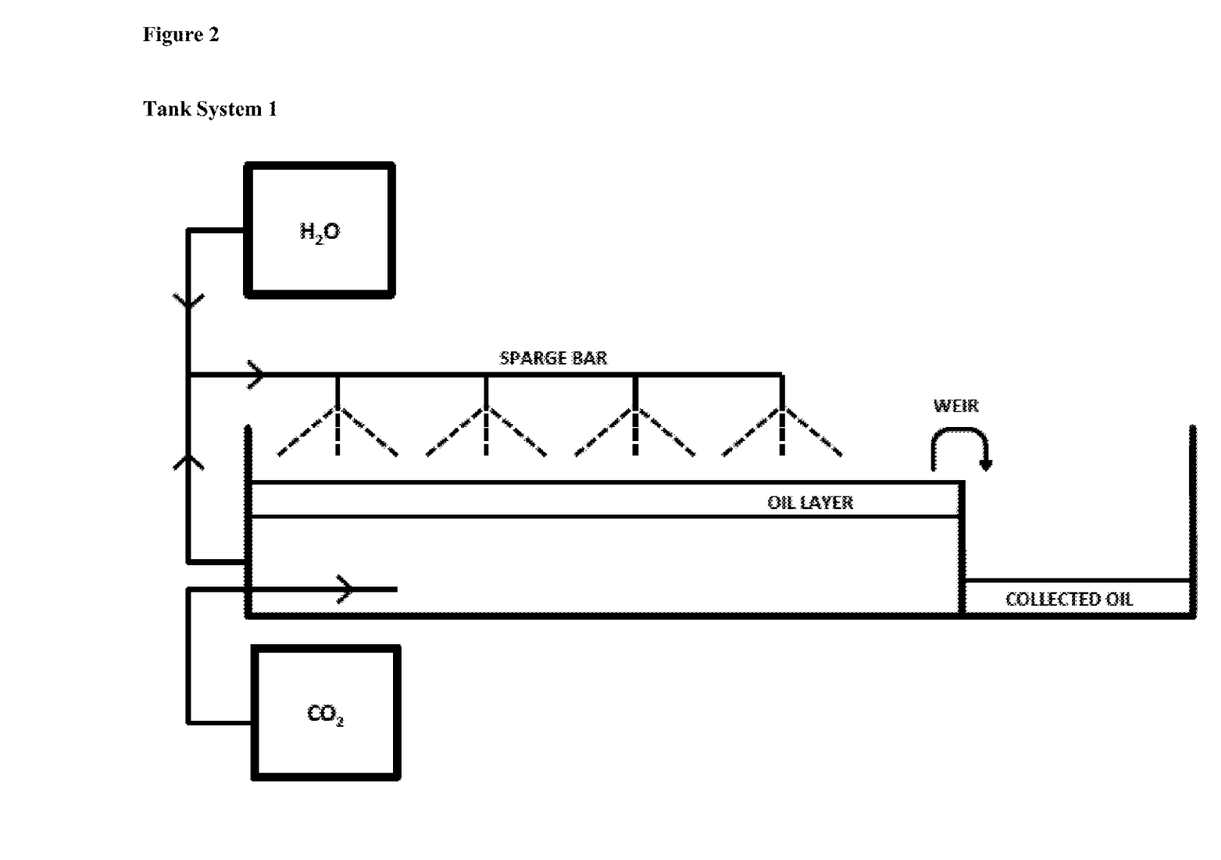
FIG. 2 shows a first tank system which can be used to produce oil according to the invention.

To initiate production of oil in the reaction tank, the larger section of the reaction vessel is filled with stock culture media. The media is then circulated until the pH has increased to between 5 and 7 and oil separates to the upper surface. The pump is then switched off.

Alternatively, to initiate production of oil in the reaction tank, the larger section of the reaction vessel is filled with stock culture media and a small quantity of oil is added to act as a primer. The oil and stock culture is mixed by circulation until an emulsion forms. Additional carbon dioxide is pumped through the reaction mixture until conversion of emulsion to oil has taken place. Conversion to oil is measured by the reduction of the level of water in the reaction mixture.

Oil may be removed from the upper surface by pulling a fat collector or boom across the upper surface, displacing the oil into the smaller of the two sections of the tank. The volume displaced is replaced by an equal volume of working culture media.

When the partition is full and the reaction is complete, the oil is pumped into an upright settling tank and allowed to stand. An anti-microbial agent is added and the water allowed to settle out. Water is removed through the lower valve.

Oil may be further processed by filtration or by removal of water to specified levels using either demulsifying filters or drying agents.

In an alternative method, 2 liters of culture medium containing 20% bacteria is mixed with disinfectant to kill the bacteria prior to commencing the production of oil. This culture medium contains the enzymes needed to convert carbon dioxide to formic acid and then to aliphatic carboxylic acids.

The culture medium containing the enzymes (and killed bacteria) is added to a reaction tank which already contains 200 liters of waste oil. 50 liters of water is then added each hour until the reaction tank contains about 2000 liters of liquid. The bacterial enzymes only produce the aliphatic carboxylic acids when the reaction tank contains more oil than water. As the enzymes produce the aliphatic carboxylic acids (in the form of an oil), the level of oil increases. As oil is produced, the level of water is increased in the tank to displace the oil into a weir. The reaction tank is replenished at intervals with further water to sustain the production of oil.

The pH of the reaction tank is maintained at about 6.5 and the temperature at about 15-20° C.

The reaction is paused at intervals to allow release of dissolved gases and for the electron balance of the system to re-equilibrate.

Once the desired lengths of aliphatic carboxylic acids have been produced in the reaction tank, oil is removed from the upper surface by pulling a fat collector or boom across the upper surface, displacing the oil into a smaller section of the reaction tank. The viscosity of the oil gives an indication of the length of the aliphatic carboxylic acids. The oil is pumped into a separate tank and any residual water removed to stop any further reactions from taking place, thereby maintaining the length of the aliphatic carboxylic acids at the desired length. An anti-microbial agent is also added before the oil is filtered.

Tank System 2

Figure 3:
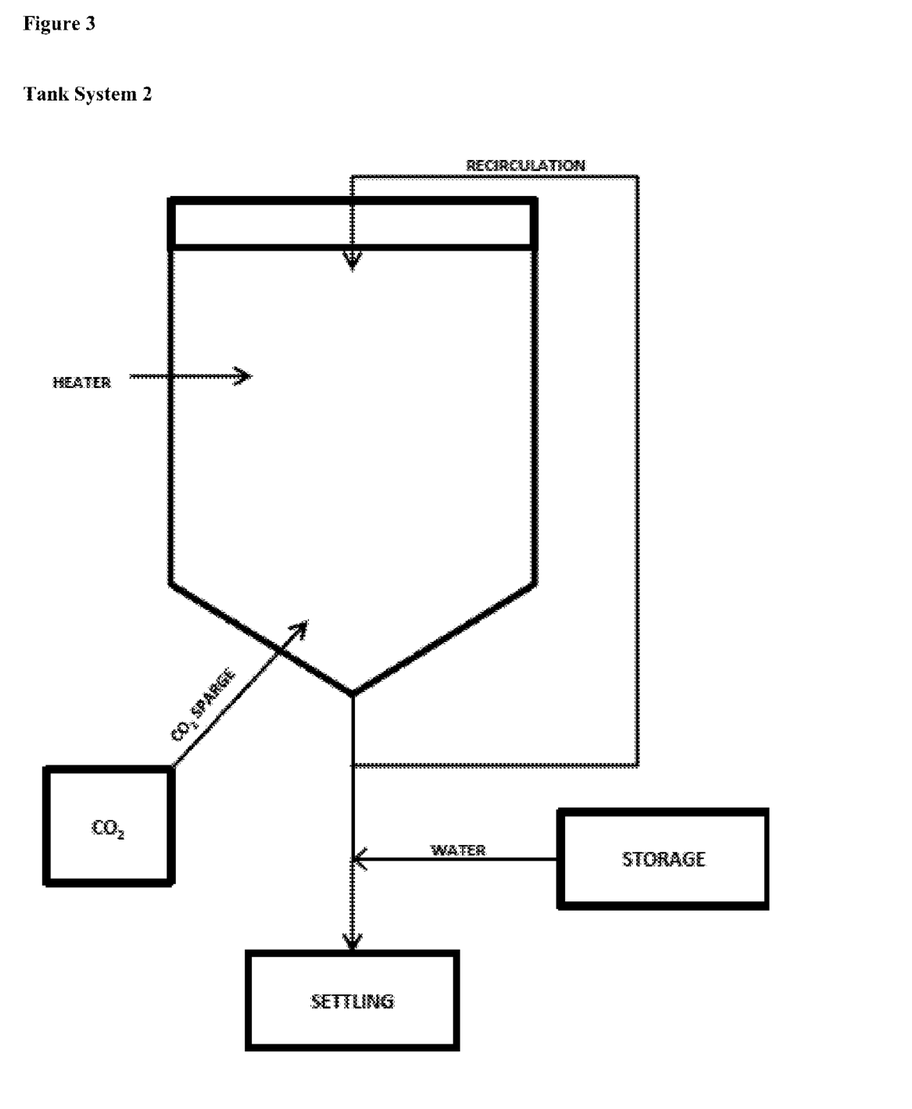
FIG. 3 shows a second tank system which can be used to produce oil according to the invention.
Figure 4:
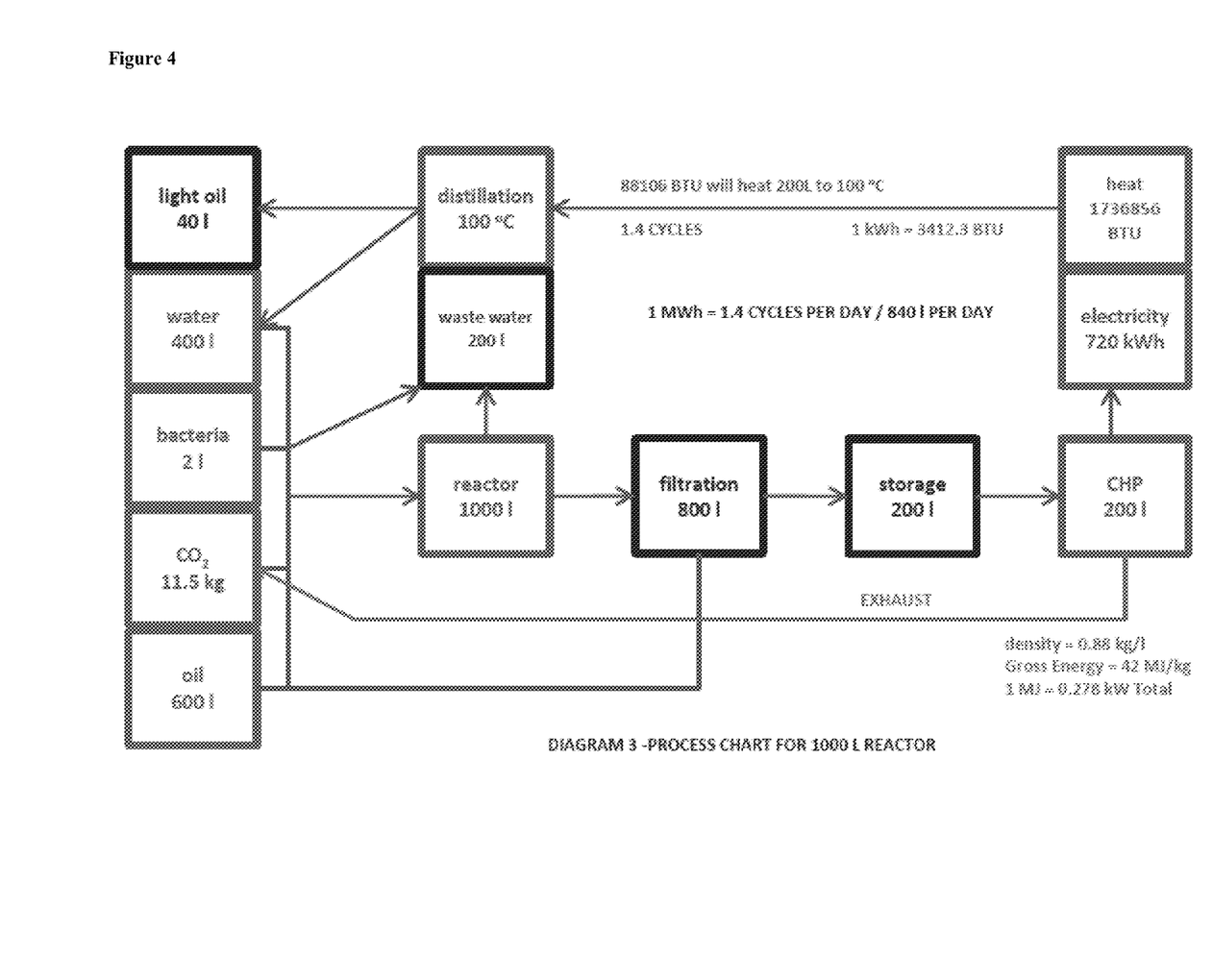
FIG. 4 is a flowchart showing the process for producing oil using the second tank system.

A second option comprises an upright mixing tank with a conical bottom, recirculation via a pump, a thermostated immersion heater and a sparge to the bottom of the tank to introduce compressed carbon dioxide gas (FIG. 3). Stock enzyme solution, a small quantity of oil to act as a primer and water are added to the tank. Optionally, a $CO_2$ sequestering agent such as triethanol amine or PEG 300 can also be added. Further, a mild oxidising agent (such as sodium hyperchlorite or sodium hydroxide) may be added to help initiate the reaction. The heater is set to a temperature of 35° C. and the contents mixed by circulation so as to form an emulsion. Carbon dioxide is introduced via the gas sparge at the bottom of the tank. The conversion of the oil-water emulsion to the aliphatic carboxylic acid oil is again followed by reduction in the level of water in the tank.

When the reaction is complete, the heat, circulation and gas flow are terminated and the contents allowed to settle. Any free water is discharged through the bottom of the tank and the oil pumped to a second settling tank via 20 micron filter. The oil is allowed to further settle to remove residual water. Waste water is either re-circulated or can be distilled to remove organic material as a light oil. (FIG. 3). Oil can be combusted through a combined heat and power engine to generate heat and electricity. Exhaust emissions from the engine can then be recycled via a scrubber unit consisting of any suitable carbon dioxide sequestering chemical, including but not limited to polyethylene glycol 300 (PEG 300).

Oil may be further processed by filtration or by removal of water to specified levels using either demulsifying filters or drying agents.

Tank systems 1 and 2 differ in the time required to form oil product. Tank system 1 is a low energy consuming option but requires extended reaction times and Tank system 2 is a more rapid technique but requires a higher energy input.

The oil is tested to specified limits.

The oil may be processed further depending on the application for which the oil is intended. In some instances, the oil may be blended with another oil, for example, in order to modify the properties/characteristics of the other oil.

The Oil Product

An oil product is obtained with the following typical values:

| ANALYSIS | UNITS | VALUE | SPECIFICATION (SUGGESTED) |
|---|---|---|---|
| Identification by IR | — | Aliphatic Carboxylic Acid | Aliphatic Carboxylic Acid |
| Ash | m/m | 0.03 | 0.025-0.050 |
| Water Content | m/m | 2.7 | 0.05 max |
| Flash Point | ° C. | 198 | 190 min |
| Viscosity @ 40° C. | cSt | 23.092 | 20-25 (50 max) |
| Viscosity Index | — | 55 | 50 min |
| Density @ 20° C. | Kg/l | 938 | 920-950 |
| Iodine Value | mg I/100 g | 90.6 | 85-95 |
| Acid Value | mg KOH/g | 147 | 140-160 |
| Peroxide Value | meg/kg | 2.9 | 3 max |
| Calorific Value Gross | MJ/kg | 38.12 | 37 min |

Alternatively, an oil product can be obtained with the following typical values:

| ANALYSIS | UNITS | VALUE | SPECIFICATION (SUGGESTED) |
|---|---|---|---|
| Identification by IR | — | Aliphatic Carboxylic Acid | Aliphatic Carboxylic Acid |
| Ash | m/m | 0.03 | 0.025-0.050 |
| Flash Point | ° C. | 105 | 100 min |
| Viscosity @ 40° C. | cSt | | 50 max |
| Density @ 15° C. | Kg/l | 0.853 | 0.85-0.882 |
| Iodine Value | mg I/100 g | 90.6 | 85-95 |
| Acid Value | mg KOH/g | 147 | 140-160 |
| Peroxide Value | meg/kg | 2.9 | 3 max |
| Oxidative Stability | H | 48+ | 48 min |
| Sulphur Content | m/m | 0.08 | 0.10 max |
| Calorific Value Gross | MJ/kg | 43.42 | 37 min |
| Cetane Index | | 50 | 50 min |
| Sediment potential | % mass/mass | <0.2 (typically 0.08) | |

Oil consists of aliphatic carboxylic acids:

The infra red fingerprint (FIG. 1) is typical of aliphatic carboxylic acids.

The oil reacts chemically as typical of a carboxylic acid.

The oil can used as short, medium or long feedstock.

The oil typically has a chain length of greater than 2 and less than 24.

The oil is typically mono unsaturated with an iodine value of 90-95 mg I/100 g.

The oil product undergoes the reactions of a carboxylic acid either as a short, medium or long chain feed stock to yield other commercially useful products. These reactions include but are not limited to:

a. Production of esters by reaction with alcohols using lipases, acid catalysts or alkali catalysts.

b. Production of amides either via the ester intermediate or directly via the Schmidt reaction.

c. Production of carboxylate salts with bases including but not exclusively alkalai hydroxides, carbonates or hydroxyl carbonates.

d. Reduction to alcohols directly by hydrogenation or via the aldehyde intermediate using catalysts including but not exclusively NN dimethylchloroethylammonium chloride and lithium aluminium hydride.

e. Reduction to aldehydes either directly by hydrogenation or via an intermediate such as the acid halide emplying the Rosenmund reduction or the thioester via the Fukuyama reduction.

f. Production of acid chlorides using reagents that include but not exclusively sulphur dichloride oxide, phosphorous (V) chloride and phosphorous trichloride g. Decarboxylation of the carboxylic acid or acid salt either enzymatically with decarboxylases or with soda lime to generate the equivalent hydrocarbon.

h. Reduction size vi the Barbier Wieland degredation.

The oil is produced directly and not by the prior production of bio mass and its subsequent processing.

The oil is not produced by fermentation.

The method of producing oil is "driven" in a novel way. The first step of the process is the reduction of carbon dioxide to produce formic acid. Formic acid is a reducing agent (redox potential −0.25). The first step of the reaction fixes carbon dioxide but also generates sufficient reducing equivalents to drive the next part of the process (chain building). The use of an "in situ" chemical battery could be used to drive other redox reactions. Formic acid (reductant) then reduces available carboxylic acids (oxidant), adding one carbon to a growing chain and releasing oxygen as $O_2$. This circumvents the need to add a reducing agent to drive the reaction, carbon and reducing equivalents being sequestered in the final product.

$$CO_2+H_2 \rightarrow HCOOH \quad \text{Step 1}$$

$$RCOOH+HCOOH \rightarrow RCH_2.COOH+O_2 \quad \text{Step 2}$$

Initial steps in chain building are enhanced by the tendency of formic acid (and most short chain carboxylic acids) to form dimers in solution.

REFERENCES (1) Qiang, L. et al. Applied Microbiology & Biotechnology (2008) pp 749-756
(2) Haas, M. J. et al. Biodiesel Handbook (2005) Eds. Knothe, G., Krahl, J. And Gerpen, J. V. AOCS Press, Urbana, Ill. pp 42-61
(3) Eliasson, B. et al. Ind Eng. Chem. Res. (1998) 37 pp 3350
(4) Wenzhein, L. Advances in Carbon Dioxide Conversion and Utilization (2010) Edit Hu, Y Am Chem Soc, Washington D.C.
(5) Howell, K. Scientific American (2009) pp 22
(6) Liao, J. C. et al. Nature Biotechnology 29 (2011) 346-351
(7) Yin, S et al, (May 1, 2012), USA Patent 2012003705
(8) McCollom, R. et al. Origins of Life and Evolution in the Biosphere (1999) 29 153-166
(9) Yoneyama, H. Catalysis Today (1997) 39 169-175
(10) Reda, T et al. PNAS (2008) 105 10654-10658
(11) Song Yin et al. (2012), US Patent 2012/0003705
(12) Simpson, S. D (2010), US Patent 2010/0317074A1
(13) Hickey, R. (2012) US Patent 2012/0003706A1
(14) Hickey, R (2012) US Patent 2012/0003707A1
(15) Kohn, R. A and Kim S-W (2012) US Patent 2012/0034664A1
(16) Worm, Petal. Microbiology (2011) 157 286-289
(17) Molinari, F., Villa, R., Aragozzini, F., Cabella, P., Barbeni, M. and Squarcia, F. J. Chem. Biotechnol. (1997) 70 294-298
(18) Fox, M. G. A, Fox, F., Dickinson, M and Ratledge, R. J. Gen. Microbiol. (1992) 138 1963-1972
(19) Tosatto, S. C. E., Toppo, S., Carbonera, D., Giacometti, G. M. and Costantini, P. Int. J. Hydrogen Energy (2008) 33 570-578
(20) Eberz, G., Hogrefe, C., Kortluke, C., Kamienski, A. And Friedrich, B. J. Bacteriol (1986) 168 636-641
(21) Ortrud Ashenbrenner and Peter Styring (2010) Energy Environmental Science 3, 1106-1113

The invention claimed is:

1. A method of producing formic acid, comprising,
contacting a culture medium comprising a micro-organism consisting of the *Acetobacter* strain having accession number NCIMB 41808, or a micro-organism derived therefrom, with carbon dioxide under conditions permitting reduction of the carbon dioxide to formic acid:

$$CO_2+H_2 \rightarrow HCOOH.$$

2. The method of claim 1, further comprising introducing a disinfectant or antimicrobial agent into the culture medium to kill the micro-organism.
3. The method of claim 2, wherein the micro-organism is killed prior to contacting the culture medium with $CO_2$.
4. The method of claim 1, wherein the culture medium comprises a minimal medium.
5. The method of claim 1, wherein carbon dioxide is the sole source of carbon.
6. The method of claim 5, wherein carbon dioxide is bubbled through the medium.
7. The method of claim 1, wherein the conditions comprise a pH of between about 3.0 and about 8.5.
8. The method of claim 7 wherein the conditions comprise a pH between about 6.0 and about 7.0.
9. The method of claim 1, wherein the conditions comprise a temperature of between about 5° C. and about 60° C.
10. The method of claim 9, wherein the conditions comprise a temperature of between about 15° C. and about 20° C.
11. The method of claim 1, wherein the medium comprises a carbon dioxide sequestering agent.
12. The method of claim 1, wherein the medium comprises an oxidising agent.
13. The method of claim 1, wherein the culture medium is an oil-water emulsion.
14. The method of claim 1, further comprising enzymatically converting the formic acid into aliphatic carboxylic acids having a chain length of five or more carbon atoms with an second enzyme system from the *Acetobacter* strain having accession number NCIMB 41808 or the micro-organism derived therefrom.
15. The method of claim 1, further comprising maintaining the amount of formic acid in the culture medium at about 20% to about 25%.
16. The method of claim 1, further comprising removing the micro-organism from the culture medium.
17. The method of claim 1, further comprising separating the formic acid from the culture medium.
18. The method of claim 1, further comprising converting formic acid to aliphatic carboxylic acids having a chain length of two or more carbon atoms.
19. The method of claim 1, further comprising chemically modifying the formic acid.

* * * * *